United States Patent

Wildman

[11] Patent Number: 4,494,931
[45] Date of Patent: Jan. 22, 1985

[54] METHOD AND PAD WITH INDEX TABS FOR APPLYING ORTHODONTIC BRACKETS

[76] Inventor: Alexander J. Wildman, 2440 Willamette St., Eugene, Oreg. 97405

[21] Appl. No.: 489,831

[22] Filed: Apr. 29, 1983

Related U.S. Application Data

[63] Continuation-in-part of Ser. No. 434,494, Oct. 15, 1982, Pat. No. 4,443,189.

[51] Int. Cl.³ ............................................... A61C 7/00
[52] U.S. Cl. ............................................. 433/8; 433/3
[58] Field of Search ......................................... 433/3, 8

[56] References Cited

U.S. PATENT DOCUMENTS 3,787,976 1/1974 Cohen .................................... 433/3
4,360,341 11/1982 Dellinger ............................... 433/3

Primary Examiner—Robert Peshock
Attorney, Agent, or Firm—Klarquist, Sparkman, Campbell, Leigh & Whinston

[57] ABSTRACT

A method applying orthodontic brackets that employ a bracket pad. The pad has a pad portion conforming to the surface of the tooth and has two laterally spaced indexing tabs integrally connected to the pad portion for bending over the tooth. An orthodontic bracket is mounted on the pad and the pad is positioned on a model of the patient's tooth so as to align the bracket as prescribed by the orthodontists. The index tabs are bent over the tooth, the pad is then burnished, and the tab ends are welded together to memorize the shape of the tooth. The pad is bonded to the patient's tooth and the index tabs are removed.

7 Claims, 5 Drawing Figures

FIG. 2
FIG. 3
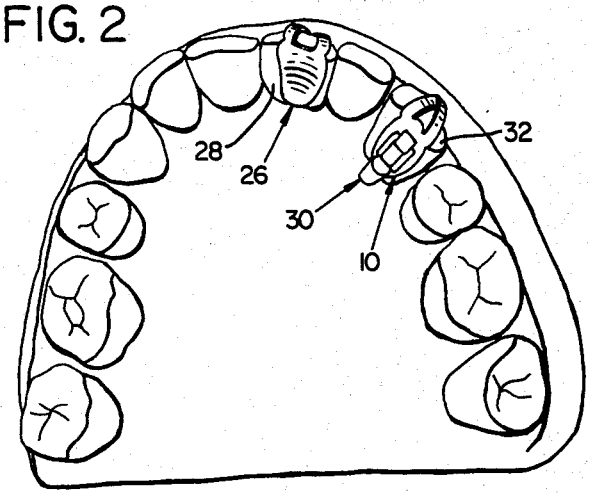
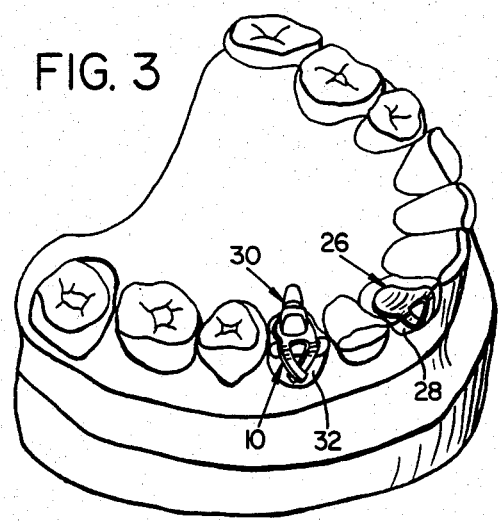
FIG. 4
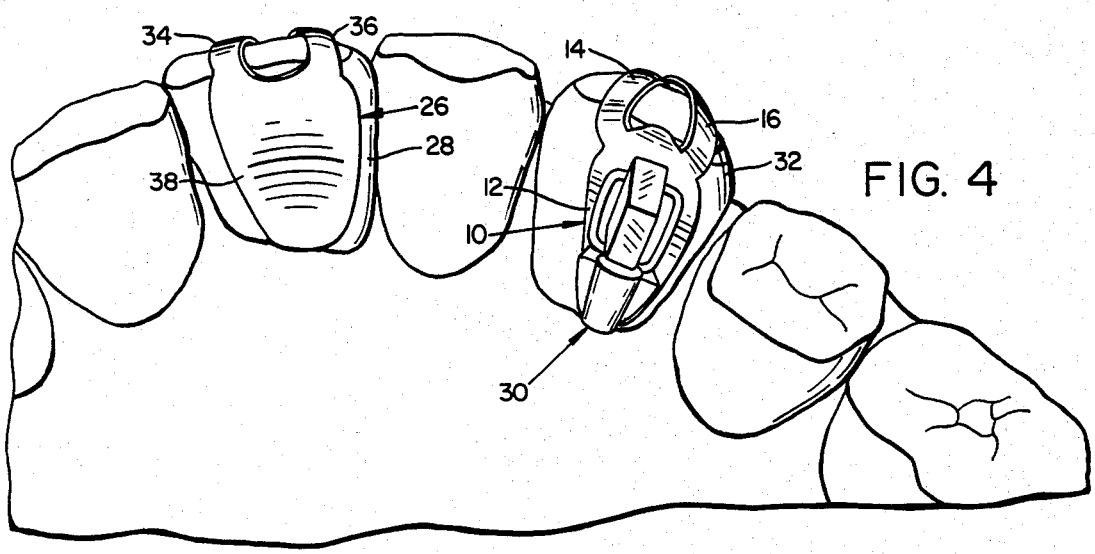
FIG. 5
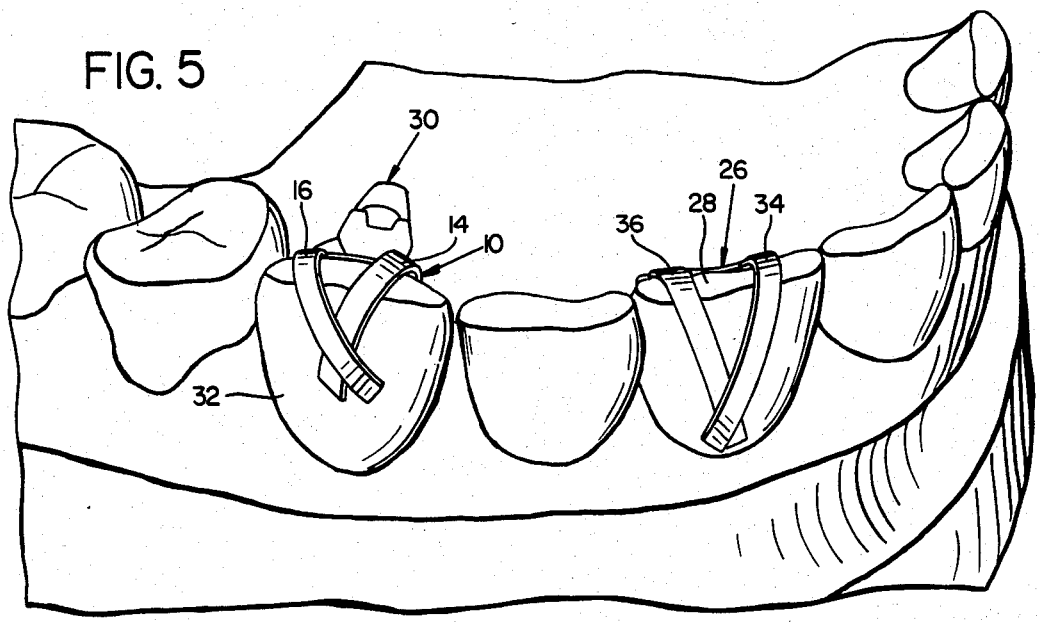

METHOD AND PAD WITH INDEX TABS FOR APPLYING ORTHODONTIC BRACKETS

This is a continuation-in-part of my copending patent application Ser. No. 06/434,494, filed Oct. 15, 1982, now U.S. Pat. No. 4,443,189 issued 4.17.84 entitled "Multipurpose Orthodontic Bracket," the subject matter of which is incorporated by reference herein.

BACKGROUND OF THE INVENTION

This invention pertains to methods and apparatus for applying orthodontic brackets to teeth.

One of the more difficult problems in applying orthodontic brackets to teeth is how to align the brackets properly with the teeth. This problem arises in the application of both lingual and labial brackets. One method of applying brackets to teeth is known in the art as the "direct" method. This method calls for simply mounting a pre-formed pad carrying a bracket directly to the tooth in the patient's mouth. "Pre-formed" means that the pad has a predetermined, usually oval, small size shape which is not altered during or after positioning the pad and bracket on a tooth. Conventionally, the pad is also substantially rigid.

Another method is the "indirect" method, which provides for pre-positioning a pre-formed pad and bracket on a plaster model of the patient's mouth. The pad is affixed to the plaster teeth with a water soluble glue. A silicone matrix is applied over the model, with the brackets mounted thereon to form a mold over the entire model. After dissolving the water soluble glue, the mold is removed from the model. Bonding cement is then applied to the pads which are exposed inside the matrix, and the entire matrix, including the brackets and pads, is fitted into the mouth. Once the bonding cement is solidified, the matrix is removed, leaving the brackets behind. Because it is so cumbersome and not as accurate as desired, this is not the technique of choice. However, it is commonly used for applying lingual brackets because the direct method is too difficult to use inside the mouth. A variation of the indirect method is applied one tooth at a time. However, the accuracy of bracket placement is still often less than optimal. The indirect techniques also cause bonding cement to be smeared onto portions of the tooth other than beneath the pad, necessitating considerable cleaning after the brackets are applied.

Accordingly, need remains for a better approach to application of orthodontic brackets to teeth.

SUMMARY OF THE INVENTION

This invention provides a method of applying orthodontic brackets that is similar to the indirect method in that it enables the initial alignment of the brackets to be conducted outside the mouth, on a plaster model of the patient's teeth. However, it differs from the conventional indirect method at the outset in not using a pre-formed rigid pad carrying a bracket. Instead, the invention comprises forming a pad to include a pad portion and indexing means connected at an occlusal end of the pad portion for bending over the occusal surface to the opposite side of the tooth. The pad is of a burnishable material, such as stainless steel foil-mesh material. The indexing means preferably comprises two, laterally-spaced, elongated tabs extending parallel to one another in a direction which will ultimately be parallel to the lengthwise axis of the tooth on which the pad is to be mounted. The method next calls for affixing an orthodontic bracket on the pad in a predetermined relationship to the tabs. The precise relationship will, of course, vary with the type of bracket which is to be used and the needs of the situation as prescribed by the orthodontist applying the bracket. The pad is then positioned on a selected tooth in a model of the patient's teeth with the index tabs extending generally parallel to the lengthwise axis of the tooth and laterally positioned on opposite sides of the axis. In this step, the pad is positioned on the tooth so as to align the bracket precisely as prescribed by the orthodontist. Next, the index tabs are bent over the occlusal surface to the opposite side of the tooth, and the pad is burnished to conform to the underlying contours of the tooth. The pad retains a memory of such contours when the bracket is removed from the model. The distal ends of the tabs may be tack welded together on the model after burnishing to fix the relative lateral positions of the index tabs. Once the position of the pad and bracket are established on the model, the bracket and pad are removed, bonding cement is applied to the underside of the pad portion, and the pad is fitted to the corresponding tooth in the patient's mouth. The contours of the tooth burnished into the pad automatically align the pad on the tooth in the patient's mouth in substantially an identical position to its position on the tooth on the model. The rigidity of the pad, when fitted on the patient's tooth, retains the pad portion carrying the bracket in contact with the underlying tooth surface until the bonding cement has solidified. Then, the index tabs are removed from the pad. The pad portion is preferably formed with boundaries conforming to the outlines of the surface of the tooth to which it is to be applied.

The foregoing and other features, objects, and advantages of the invention will become more readily apparent from the following detailed description which proceeds with reference to the accompanying drawings.

BRIEF DESCRIPTION OF THE DRAWINGS

FIGS. 2 and 3 are perspective views of the lingual and labial sides, respectively, of a plaster model showing an incisor pad in accordance with the invention positioned on one tooth and an upper cuspid pad with a bracket positioned on another tooth.

FIGS. 4 and 5 are close-up perspective views of the subject matter of FIGS. 2 and 3.

DETAILED DESCRIPTION

Figure 1:
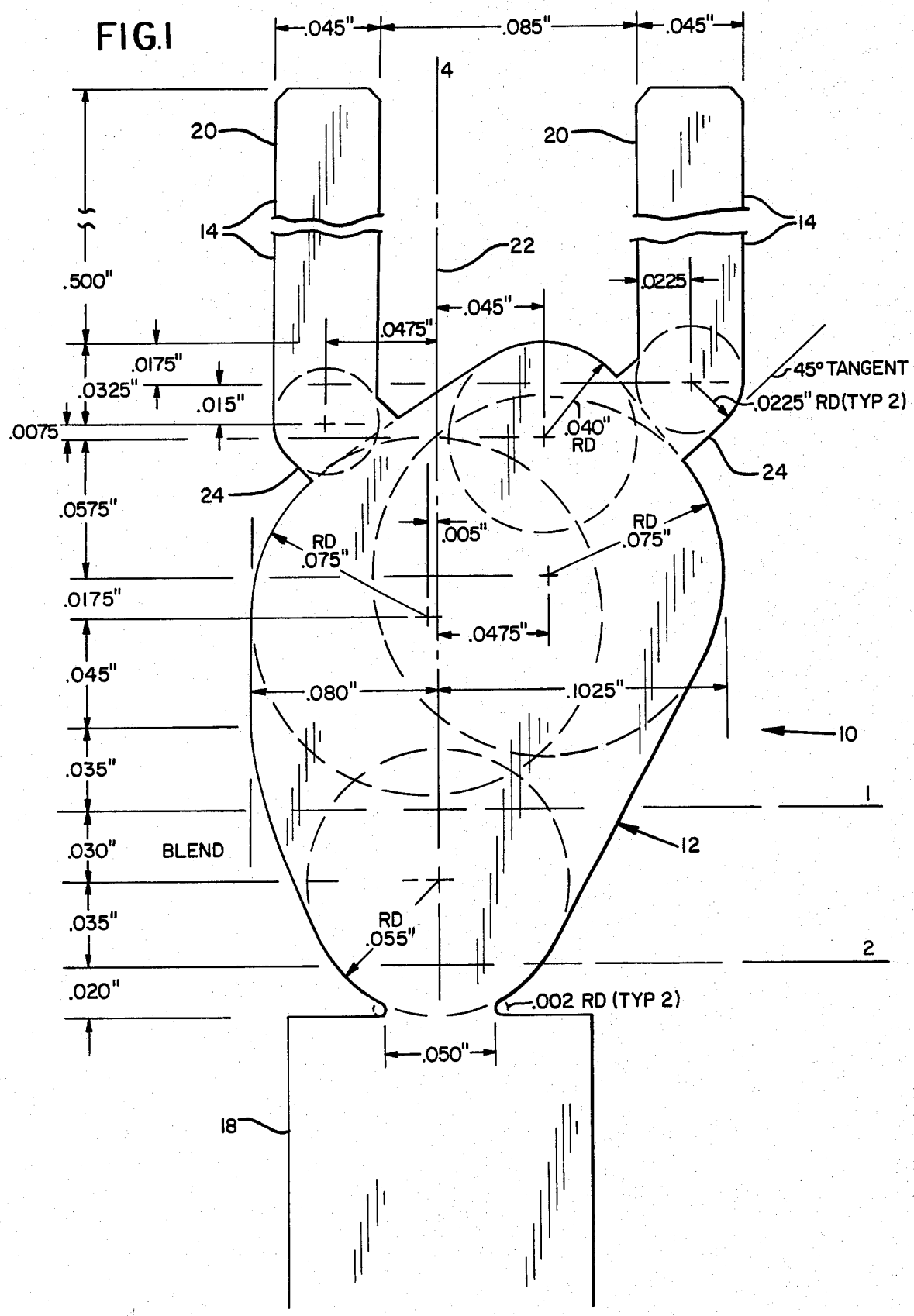
FIG. 1 is a plan view of an upper cuspid pad in accordance with the invention.

Referring to FIG. 1, an orthodontic bracket pad 10, in this particular example an upper cuspid pad, comprises a pad portion 12 and a pair of index tabs 14, 16 positioned at an upper or occlusal end of the pad portion. For ease of handling during manufacture, the pad includes a rectangular tooling tab 18 connected to the lower or gingival end of the pad portion 12. Pad 10 is integrally formed either by etching or by stamping the pad in accordance with the boundaries defining the pad portion, index tabs and tooling tab, from a burnishable pad material, such as 300 Series stainless steel mesh-foil pad material.

The pad portion 12 has a perimeter contoured to conform to the general shape of the surface of the tooth to which the pad is to be applied. In this example, the pad is to be used on the lingual side of an upper cuspid and contoured accordingly. For application of the invention to other teeth, or to the labial surfaces thereof, the shape of the pad portion 12 is altered accordingly, as exemplified in FIGS. 2-5 by incisor pad 26.

The index tabs 14, 16 each include an elongated, generally rectangular distal portion 20, both extending substantially parallel to an axis 22 corresponding to the axis of the tooth on which the pad is to be mounted. As indicated in the drawing, a suitable length of such distal portions is about one-half inch. The distal portions are spaced apart, for example, 0.085 inch apart, on opposite sides of axis 22. As will be further described hereinafter, this spacing enables the tabs to be bent over the occlusal surface of the tooth in such a way that the end portions cross on the opposite side of the tooth, thereby aiding in defining and memorizing unique contours of the tooth.

The index tabs are integrally connected to pad portion 12, in the case of a cuspid pad, through short proximal portions 24 which extend outwardly from the pad portion at forty-five degree angles from axis 22 and at right angles to one another. Such portions are of sufficient length to provide the desired spacing between portions 22. They can be omitted on pads of suitably wide conformation, such as that of the pad portion of incisor pad 26 shown mounted on an incisor 28 in a plaster model illustrated in FIGS. 4-5, wherein index tabs 34, 36 connect directly to the pad portion 38.

Continuing to refer to the FIGS. 2-5, cuspid pad 10 has a bracket 30 mounted on pad portion 12 overlying the lingual surface of tooth 32. The particular form of bracket illustrated in FIGS. 2-5 is the base portion of a bracket described fully in my aforementioned U.S. patent application. The underside of the base portion of the bracket is welded to the upper surface of pad portion 12.

Initially, the index tabs are straight. To fix or memorize the position of the pad portion on the tooth 32 of the model in the position prescribed the orthodontist, the index tabs 14, 16 are bent forwardly over the occlusal surface of tooth 32 and downwardly along the frontal or labial surface thereof. The pad portion 12 is burnished to conform to the underlying contours of the inner or labial surface of tooth 32. The index tabs are likewise burnished to conform to the occlusal and labial surfaces thereof.

Referring to FIG. 5, it can be seen that the index tabs cross on the labial side of the teeth. Once the burnishing is complete, the tabs are preferably spot-welded together at the intersection so as to more securely retain their relative position in conformity with the shape of the tooth. It should be understood that the orthodontist will position the pad on the tooth in accordance with a prescription appropriate to the needs of the particular patient. The pad portion and index tabs are burnished by rubbing their surfaces under pressure with a blunt-pointed tool, and the index tabs tack-welded at their intersection, to memorize the position prescribed by the orthodontist, so that the bracket and pad can be transferred to substantially identically the same position on the patient's corresponding tooth.

The entire pad, carrying the bracket, is then removed from the model. Bonding cement is applied to the mesh underside of the pad portion. Then the pad and bracket are transferred to the patient's mouth, where the pad is fitted on the patient's corresponding tooth. As the pad is pressed down on the tooth, the tooth shape burnished into the pad portion and index tabs guides the pad into a position substantially identical to that obtained on the plaster model. Once seated on the tooth, the index tabs assist in retaining the pad portion in close contact with the lingual surface of the tooth while the bonding cement solidifies. Subsequently, the index tabs are removed at the upper or occlusal edge of the pad portion. Any rough edges in the pad are likewise smoothed out for the comfort of the patient.

Having illustrated and described the principles of my invention in a preferred embodiment, with specific examples thereof, it should be appreciated that the invention can be modified in arrangement and detail without departing from such principles. I claim all modifications coming within the scope of the following claims:

I claim:

1. An orthodontic bracket mounting pad comprising:
   a generally planar pad portion having a perimeter contoured to conform generally to the shape of one of a lingual and labial surface of a selected tooth, the pad portion having a gingival end and an occlusal end, and
   indexing means integrally connected to the occlusal end of the pad portion and extending outwardly therefrom for a sufficient length to be bent over the occlusal surface of the tooth to the opposite side of the tooth from said one surface;
   the pad portion and indexing means being formed of a burnishable material so that the pad can be burnished to substantially conform to the underlying contours of the selected tooth in a plaster model and thereby memorize such shape so that the pad can be transferred to substantially identically the same position on the corresponding tooth of the patient from whom the model was made.

2. A pad according to claim 1 in which the indexing means comprises a pair of elongated index tabs extending substantially parallel to a selected axis corresponding to the axis of the tooth on which the pad is to be mounted and spaced laterally apart about said axis.

3. A pad according to claim 2 in which the index tabs have a length such that, when bent to the opposite side of the tooth from that on which the pad portion is mounted, the index tabs cross.

4. A pad according to claim 3 in which the pad portion and index tabs are integrally formed of stainless steel mesh-foil pad material.

5. A method of applying an orthodontic bracket to a tooth comprising:
   forming a bracket pad of a burnishable pad material, the pad including a pad portion having a perimeter contoured to fit one of a labial and lingual side of a selected tooth and indexing means integrally connected to the pad portion and extending beyond said perimeter from an occlusal end of the pad portion;
   affixing a bracket to an upper side of the pad portion;
   positioning the pad on a tooth in a model with the bracket in a predetermined position and an underside of the pad portion contacting an underlying surface of the tooth of the model;
   burnishing at least the indexing means to conform to the underlying shape of the tooth so as to memorize the position of the bracket thereon;
   transferring the pad and bracket to the corresponding tooth of the patient and fitting the pad thereon with the pad portion in a position determined by the burnished indexing means thereby to replicate the memorized position of the bracket on the model;
   bonding the pad portion to the patient's tooth; and
   cutting the indexing means off of the pad portion.

6. A method according to claim 5 in which the burnishable material includes a thin metal sheet, the indexing means is formed to define a pair of parallel indexing tabs sized and arranged so as to cross on the opposite side of the tooth from which the pad portion is positioned, the method further including tack-welding of the indexing tabs at their intersection.

7. A method according to claim 5 including burnishing the pad portion.

* * * * *